US00PP30597P3

(12) United States Plant Patent
Berry

(10) Patent No.: US PP30,597 P3
(45) Date of Patent: Jun. 25, 2019

(54) ***HIBISCUS* PLANT NAMED 'JBG 14006'**

(50) Latin Name: *Hibiscus rosa-sinensis*
Varietal Denomination: JBG 14006

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 15/998,307

(22) Filed: Aug. 2, 2018

(65) Prior Publication Data

US 2019/0045692 P1 Feb. 7, 2019

Related U.S. Application Data

(60) Provisional application No. 62/605,169, filed on Aug. 3, 2017.

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
See application file for complete search history.

*Primary Examiner* — Annette H Para
(74) *Attorney, Agent, or Firm* — The Webb Law Firm

(57) ABSTRACT

A new and distinct *Hibiscus* plant having light red colored flowers with overlapping, ruffled flower petals that last for several days on the plant over a long flowering season.

1 Drawing Sheet

Botanical classification: *Hibiscus rosa-sinensis.*
Varietal denomination: 'JBG 14006'.

BACKGROUND OF THE INVENTION

The present invention comprises a new and distinct *Hibiscus* plant having the varietal name 'JBG 14006'. The new variety is the result of a planned breeding program with the purposes of developing *Hibiscus rosa-sinensis* plants that exhibit pathogen resistance, multi-day flowers with unique coloration, and possess desirable production traits. 'JBG 14006' is the result of a cross conducted in Grand Saline, Tex. between *Hibiscus rosa-sinensis* varieties 'JBN 12002' (female parent, U.S. Plant Pat. No. 27,304) and 'JBG 12020' (male parent, unpatented). The new variety was selected in October of 2013 in Grand Saline, Tex. and the first asexual reproduction of the new variety was conducted by semi-mature, softwood cuttings in September of 2014 in Grand Saline, Tex. 'JBG 14006' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG 14006' is similar to its female parent in having red colored flowers with a shrub growth habit, but differs from its female parent in having smaller flowers that are a lighter shade of red and an increased bud count. 'JBG 14006' is similar to its male parent in flower size and bud count, but differs from its male parent in flower color ('JBG 12020' has yellow colored flowers) and 'JBG 14006' exhibits higher vigor.

When 'JBG 14006' is compared to *Hibiscus rosa-sinensis* variety 'JBG 14025' (U.S. Plant patent application Ser. No. 15/998,306), both varieties exhibit overlapping and ruffled petals. However, the petals of 'JBG 14006' are more ruffled in appearance than 'JBG 14025' and the flowers of 'JBG 14006' are red in color, while the flowers of 'JBG 14025' are orange in color.

The following traits distinguish 'JBG 14006' as a new and distinct cultivar from other *Hibiscus* varieties known to the breeder:

1. Light red colored flowers;
2. Overlapping flower petals with a ruffled appearance;
3. Resistance to bacterial leaf spot (*Pseudomonas* spp.); and
4. Multi-day flowers.

DESCRIPTION OF THE DRAWING

The accompanying photographic image illustrates the new variety at approximately one year of age, with the colors being as nearly true as is possible with color illustrations of this type:

FIG. 1 illustrates a close-up view of a flower of the new variety.

DESCRIPTION OF THE PLANT

The following detailed description sets forth the characteristics of the new variety. The color readings and measurements were taken in the summer in Grand Saline, Tex. under natural light on approximately one year old, growing plants in 24.0 cm diameter containers. Color references are primarily to The 1995 R.H.S. Colour Chart of The Royal Horticultural Society of London, 3$^{rd}$ Edition, except where general color terms are used.

PLANT

Time to initiate roots: About 48 days at an average of 24° C.

Time to develop roots: About 55 days at an average of 24° C.

Time to produce a finished flowering plant from a rooted cutting: About 30 weeks in a 24.0 cm diameter container.

Specific disease/pest resistance: Resistance to bacterial leaf spot (*Pseudomonas* spp.).

Heat/cold tolerance: Nothing unusual noted to date.

Drought tolerance: Nothing unusual noted to date.

Plant:

*Type*.—Tropical, ornamental shrub.

*Habit*.—Upright.

*Height*.—90.0 cm at maturity.

*Spread*.—60.0 cm at maturity.

*Vigor*.—Moderate.

Rooting vigor: Strong.

Stem:

*Number per plant*.—7.

*Length*.—Ranging from 35.0-49.0 cm.

*Width*.—5.0 mm.

*Texture*.—Immature: Smooth. Mature: Vertically ridged.

*Strength*.—Moderate.

*Branch number*.—Moderate; 7.

*Internode length*.—2.0-2.5 cm.

*Color*.—Immature: 144A. Mature: 177B.

*Stipules*.—Number per node: 2. Shape: Linear. Length: 8.0 mm. Width: 1.0 mm. Surface texture: Smooth. Base: Linear. Margin: Entire. Color: 144C.

Foliage:

*Arrangement*.—Alternate.

*Size of leaf*.—Length: 6.0 cm. Width: 5.5 cm.

*Shape of leaf* (*generally*).—Ovate.

*Shape of apex*.—Acute.

*Shape of base*.—Rounded.

*Texture* (*both surfaces*).—Smooth.

*Margin type*.—Crenate to undulate.

*Color*.—Young leaves: Upper surface: 143A. Lower surface: 143C. Mature leaves: Upper surface: 138A. Lower surface: 139B.

*Veins*.—Venation type: Pinnate. Color: Upper surface: 143B. Lower surface: 142D.

*Petiole*.—Length: 3.0-4.0 cm. Diameter: 3.0 mm. Texture: Smooth. Color: 143B.

FLOWERS

Buds (described at immaturity):

*Shape*.—Acute.

*Diameter*.—5.0 mm.

*Length*.—1.0 cm.

*Color*.—143C.

Natural flowering season: From spring through fall in Grand Saline, Tex.

Flower type and habit: Single, with overlapping petals.

Fragrance: None observed.

Flowers (described on the first day of opening):

*Number per stem*.—1.

*Overall depth*.—14.0 cm.

*Overall diameter*.—8.0 cm.

*Shape*.—Rotate; regular.

*Lastingness*.—2-3 days on the plant.

*Petals*.—Number: 5. Arrangement: Simple. Length: 7.4 cm. Width: Apex: 7.0 cm. Base: 3.5 cm. Shape: Ovate. Apex: Obtuse. Base: Cuneate. Margin: Entire. Texture/appearance: Upper surface: Smooth. Lower surface: Smooth. Color: When opening and fully opened: Upper surface: 168A at the apex to 44A then to 178A at the throat. Lower surface: 162A at the apex to 180B at the base.

*Calyx*.—Form: Fused. Overall length: 2.8 cm. Overall diameter: 1.8 cm. Sepals/calyx lobes: Number: 5. Shape: Acute. Apex: Acuminate. Margin: Entire. Texture: Slightly pubescent. Color: Outer surface: 143B. Inner surface: 143C.

*Epicalyx*.—Length: 1.0 cm. Width: 3.0 mm. Texture: Smooth. Color: 143A.

*Bracts*.—Not present.

*Peduncle*.—Length: 4.5 cm. Diameter: 3.0 mm. Strength: Strong. Angle: 20°. Texture: Smooth. Color: 144B.

Reproductive organs:

*Gynoecium*.—Pistils: Number: 1. Length: 8.0 cm. Stigma: Number: 5. Shape: Round. Length: 5.0 mm. Diameter: 1.0 mm. Color: 146A. Style: Length: 6.0 cm. Width: Apex: 3.0 mm. Base: 5.0 mm. Color: 16B. Ovary: Shape: Ovate. Length: 1.0 cm. Width: 5.0 mm. Color: 10C.

*Androecium*.—Stamens: Number: 63. Position: Just below the stigma on the style. Anther: Shape: U-shaped. Diameter: 1.0 mm. Color: 12A. Filament: Length: 3.0 mm. Width: 1.0 mm. Color: 42C. Pollen: Color: 12A. Amount (generally): Moderate.

SEEDS

Seeds:

*Number*.—From 0 to 20.

*Color*.—200C.

*Length*.—5.0 mm.

*Width*.—5.0 mm.

I claim:

1. A new and distinct variety of *Hibiscus* plant, as is herein illustrated and described.

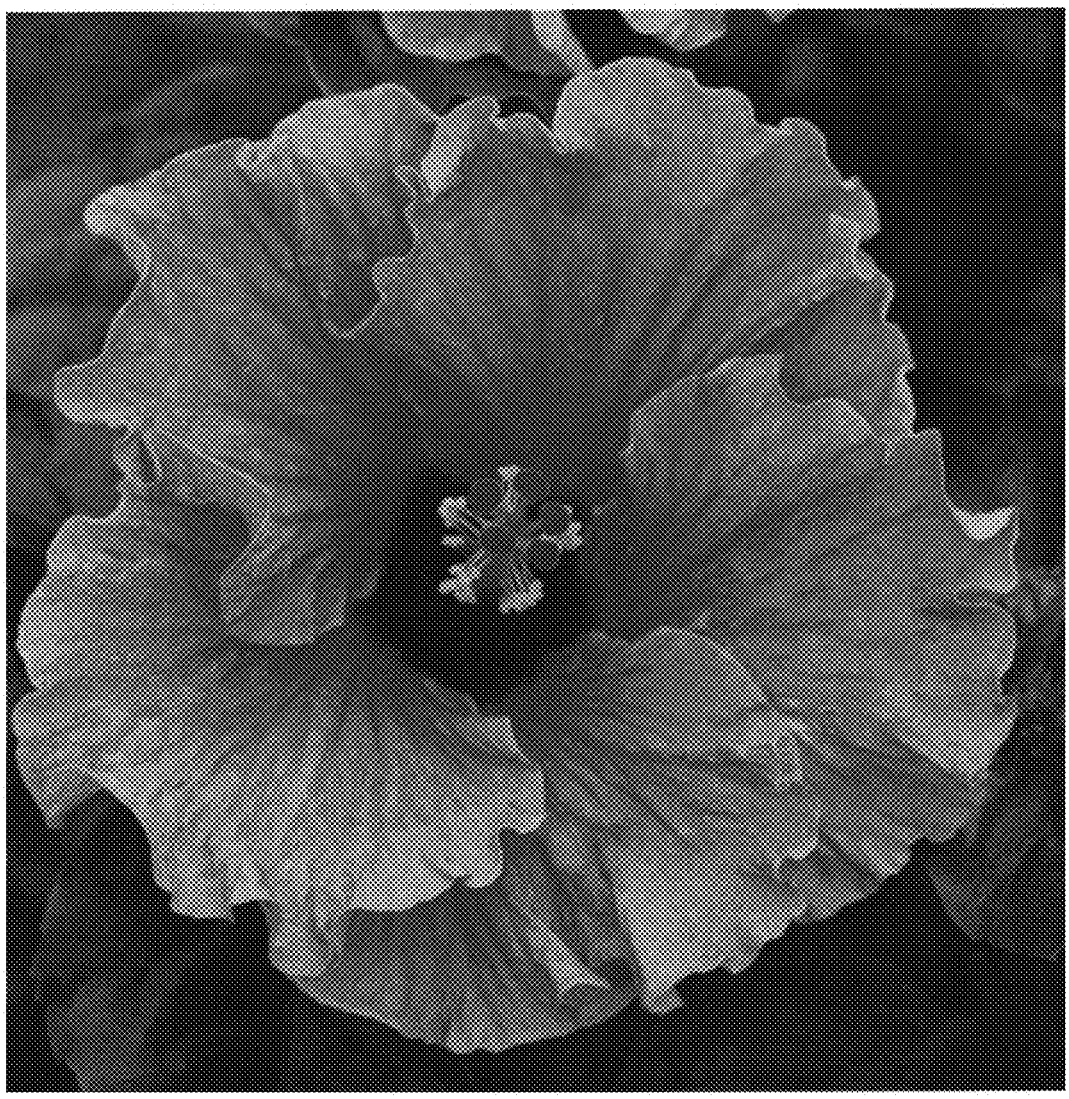

* * * * *